United States Patent
Zhang et al.

(10) Patent No.: US 11,376,267 B2
(45) Date of Patent: Jul. 5, 2022

(54) DRUG COMBINATION FOR TREATMENT OF AMYOTROPHIC LATERAL SCLEROSIS, PREPARATION METHOD AND USE THEREOF

(71) Applicant: SICHUAN JIUZHANG BIOLOGICAL SCIENCE AND TECHNOLOGY CO., LTD., Sichuan (CN)

(72) Inventors: Jie Zhang, Sichuan (CN); Xiaoguang Chen, Sichuan (CN); Huarong Yang, Sichuan (CN); Wenbin Li, Sichuan (CN)

(73) Assignee: SICHUAN JIUZHANG BIOLOGICAL SCIENCE AND TECHNOLOGY CO., LTD., Sichuan (CN)

( * ) Notice: Subject to any disclaimer, the term of this patent is extended or adjusted under 35 U.S.C. 154(b) by 103 days.

(21) Appl. No.: 16/772,717

(22) PCT Filed: Jun. 28, 2019

(86) PCT No.: PCT/CN2019/093794
§ 371 (c)(1),
(2) Date: Jun. 12, 2020

(87) PCT Pub. No.: WO2020/019938
PCT Pub. Date: Jan. 30, 2020

(65) Prior Publication Data
US 2021/0137951 A1    May 13, 2021

(30) Foreign Application Priority Data
Jul. 24, 2018   (CN) .................. 201810814892.7

(51) Int. Cl.
| | |
|---|---|
| *A61K 31/661* | (2006.01) |
| *A61P 25/28* | (2006.01) |
| *A61K 9/00* | (2006.01) |
| *A61K 9/19* | (2006.01) |
| *A61K 9/20* | (2006.01) |
| *A61K 9/48* | (2006.01) |
| *A61K 31/122* | (2006.01) |
| *A61K 31/216* | (2006.01) |
| *A61K 31/355* | (2006.01) |
| *A61K 31/375* | (2006.01) |

(52) U.S. Cl.
CPC .......... *A61K 31/661* (2013.01); *A61K 9/0019* (2013.01); *A61K 9/19* (2013.01); *A61K 9/20* (2013.01); *A61K 9/48* (2013.01); *A61K 31/122* (2013.01); *A61K 31/216* (2013.01); *A61K 31/355* (2013.01); *A61K 31/375* (2013.01); *A61P 25/28* (2018.01)

(58) Field of Classification Search
CPC .. A61K 31/122; A61K 31/216; A61K 31/355; A61K 31/661; A61K 9/0019; A61K 9/1652; A61K 9/19; A61K 9/20; A61K 9/2054; A61K 9/48; A61K 31/375; A61P 25/28
See application file for complete search history.

(56) References Cited

U.S. PATENT DOCUMENTS

| | | | | |
|---|---|---|---|---|
| 7,285,573 | B2 * | 10/2007 | Kaddurah-Daouk | ................... A61K 31/675 514/565 |
| 2008/0233245 | A1 * | 9/2008 | White | ............... A23L 33/175 426/73 |

FOREIGN PATENT DOCUMENTS

| | | |
|---|---|---|
| CN | 103520190 A | 1/2014 |
| CN | 104622863 A | 5/2015 |
| CN | 108771668 A | 11/2018 |
| WO | WO 2016127399 | * 8/2016 |

OTHER PUBLICATIONS

Wang, CN 104622863A, see English translation (Year: 2015).*
University of Washington Medical Center (Patient Education, Univ of Washington Medical Center, 2001) (Year: 2001).*

* cited by examiner

*Primary Examiner* — Umamaheswari Ramachandran
(74) *Attorney, Agent, or Firm* — Novick, Kim & Lee, PLLC; Allen Xue

(57) ABSTRACT

A drug combination for treatment of amyotrophic lateral sclerosis includes chlorogenic acid, vitamin E, vitamin C, coenzyme Q10, and creatine phosphate sodium, as well as pharmaceutically acceptable carriers, in which chlorogenic acid, vitamin E, vitamin C, coenzyme Q10, and creatine phosphate sodium are unit preparations having same or different specifications, that are simultaneously or separately administrated. The combination of chlorogenic acid, vitamin E, vitamin C, coenzyme Q10, and creatine phosphate sodium shows a synergistic effect on amyotrophic lateral sclerosis, thus provides a combination with excellent therapeutic effect on amyotrophic lateral sclerosis, which delays the progression of amyotrophic lateral sclerosis.

7 Claims, No Drawings

DRUG COMBINATION FOR TREATMENT OF AMYOTROPHIC LATERAL SCLEROSIS, PREPARATION METHOD AND USE THEREOF

TECHNICAL Field

The present invention belongs to the medicinal field, and particularly relates to a drug combination for treatment of amyotrophic lateral sclerosis as well as the preparative method and the use thereof.

BACKGROUND ART

Amyotrophic lateral sclerosis (ALS) is also called motor neuron disease (MND), with as trivial name "gradually frozen disorder", prone to occur in men, and the age of onset is generally 40-70 years old. ALS is a neurodegenerative disease caused by progressive degeneration of motor neurons in the cerebral cortex, brain stem and spinal cord, leading to muscle weakness and atrophy, as well as speech, swallowing, and respiratory dysfunction. Although there are rather obvious individual differences in the clinical manifestations and the progression rate of the disease, without exception, the disease of patients is gradually worsening. More than 60% of patients die within 3 years of onset, and about 10% of patients have a survival time of≥8 years. Most of patients with amyotrophic lateral sclerosis (ALS) don't have clear genetic causes, and 5-10% of ALS patients are familial, while additional 90-95% of patients don't have a family history and are sporadic. Current research have indicated that except for relationship with heredity, the occurrence of amyotrophic lateral sclerosis (ALS) also has certain correlation with multiple factors such as neuroinflammatory response, mitochondrial dysfunction, protein aggregation, autoimmunity, retroviral infection and so on, and based on these, oxidative free radical theory, immunological theory, nerve growth factor deficiency theory, excitatory amino acid toxicity theory and so on are developed, but the exact causes and pathogenesis are still unclear at present.

For amyotrophic lateral sclerosis (ALS), drugs delaying the development of the disease are mainly administered in clinical, such as edaravone, riluzole, etc. Currently, other therapeutic methods for amyotrophic lateral sclerosis (ALS), such as antisense therapy, gene therapy, and stem cell therapy, are still on the exploration stage, and have not been used in clinical. Thus, the effective therapeutic methods for amyotrophic lateral sclerosis (ALS) are still absent.

Chlorogenic acid (CGA), also called coffee tannic acid is a condensed phenolic acid formed by condensation of caffeic acid (CA) and quinic acid (QA), with a chemical name of 3-O-caffeoylquinic acid (CGA). It has lots of activities, such as cardiovascular protection, anti-oxidation, anti-ultraviolet and anti-radiation, anti-mutagenesis, anti-cancer, anti-bacterial, antiviral, lipid-lowering, glucose-lowering, immune regulation, etc. It has been reported that chlorogenic acid has certain therapeutic effect on amyotrophic lateral sclerosis (ALS), but the effect is still not as expected.

Based on the prior art, the present invention has thoroughly researched the therapeutic effect of chlorogenic acid on amyotrophic lateral sclerosis (ALS), and directs at providing an therapeutic drug with excellent effects on amyotrophic lateral sclerosis (ALS).

Content of the Present Invention

The objective of the present invention is to provide a drug combination for treatment of amyotrophic lateral sclerosis, characterized in that the combination includes chlorogenic acid, vitamin E, vitamin C, coenzyme Q10, and creatine phosphate sodium, as well as pharmaceutically acceptable carriers.

Preferably, said chlorogenic acid, vitamin E, vitamin C, coenzyme Q10, and creatine phosphate sodium are unit preparations having same or different specifications, that are simultaneously or separately administrated.

Preferably, the weight ratio of chlorogenic acid, vitamin E, vitamin C, coenzyme Q10, and creatine phosphate sodium is 100-300:100-500:75-600:100-600:500-2500.

Preferably, the weight ratio of chlorogenic acid, vitamin E, vitamin C, coenzyme Q10, and creatine phosphate sodium is 150-250:250-400:200-400:200-400:800-2000.

Preferably, the weight ratio of chlorogenic acid, vitamin E, vitamin C, coenzyme Q10, and creatine phosphate sodium is 180:300:300:300:1000.

Preferably, said vitamin E is α-tocopheryl polyethylene glycol succinate, while said coenzyme Q10 is selected from liposoluble coenzyme Q10 or water-soluble coenzyme Q10.

Said drug combination is preferable to be oral or injective preparations, and preferably, the oral forms are selected from the group consisting of tablet, capsule, granule, pill, powder, solid dispersion, and oral liquid, while said injectable forms are selected from injection or lyophilized powder injection.

Said pharmaceutically acceptable carriers are selected from diluents, binders, disintegrants, lubricants or glidants, flavoring agents, coatings, gelatin capsule shells, solvents, lyophilization protectants, etc.

Said diluents are selected from starch, dextrin, microcrystalline cellulose, etc.; said binders are selected from starch syrup, hydroxypropylmethylcellulose, sodium carboxymethyl cellulose, povidone, etc.; said disintegrants are selected from sodium carboxymethyl starch, crospovidone, croscarmellose sodium, etc.; said lubricants or glidants are selected from magnesium stearate, talc, micronized silica gel, etc.; said solvents are selected from water, injectable water, etc.; said lyophilization protectants are selected from mannitol, etc.

In the drug combination for treatment of amyotrophic lateral sclerosis according to the present invention, active ingredients chlorogenic acid, vitamin E, vitamin C, coenzyme Q10, and creatine phosphate sodium are 1-99% of total weight of the drug combination; preferably, in the drug combination, active ingredients chlorogenic acid, vitamin E, vitamin C, coenzyme Q10, and creatine phosphate sodium are 5-25% of total weight of the drug combination; most preferably, in the drug combination, active ingredients chlorogenic acid, vitamin E, vitamin C, coenzyme Q10, and creatine phosphate sodium are 15% of total weight of the drug combination.

The dosage of the drug combination for treatment of amyotrophic lateral sclerosis according to the present invention is 1-100 mg/kg body weight, preferably 5-60 mg/kg body weight, and most preferably 20 mg/kg body weight.

Another objective of the present invention is to provide the preparative method of the drug combination for treatment of amyotrophic lateral sclerosis: the combination is prepared by using chlorogenic acid, vitamin E, vitamin C, coenzyme Q10, and creatine phosphate sodium as active ingredients, together with addition of pharmaceutically acceptable carriers.

Preferably, the drug combination is oral or injectable preparations.

Said pharmaceutically acceptable carriers are selected from the group consisting of diluents, binders, disintegrants, lubricants or glidants, flavoring agents, coatings, gelatin capsule shells, solvents, lyophilization protectants, etc.

Said diluents are selected from starch, dextrin, microcrystalline cellulose, etc.; said binders are selected from starch syrup, hydroxypropylmethylcellulose, sodium carboxymethyl cellulose, povidone, etc.; said disintegrants are selected from sodium carboxymethyl starch, crospovidone, croscarmellose sodium, etc.; said lubricants or glidants are selected from magnesium stearate, talc, micronized silica gel, etc.; said solvents are selected from water, injectable water, etc.; said lyophilization protectants are selected from mannitol, etc.

Further objective of the present invention is to provide the use of the combination of chlorogenic acid, vitamin E, vitamin C, coenzyme Q10, and creatine phosphate sodium in the preparation of drug compositions for treatment of amyotrophic lateral sclerosis.

Preferably, the weight ratio of chlorogenic acid, vitamin E, vitamin C, coenzyme Q10, and creatine phosphate sodium is 100-300:100-500:75-600:100-600:500-2500.

More preferably, the weight ratio of chlorogenic acid, vitamin E, vitamin C, coenzyme Q10, and creatine phosphate sodium is 150-250:250-400:200-400:200-400:800-2000.

Most preferably, the weight ratio of chlorogenic acid, vitamin E, vitamin C, coenzyme Q10, and creatine phosphate sodium is 180:300:300:300:1000.

Preferably, said vitamin E is α-tocopheryl polyethylene glycol succinate, while said coenzyme Q10 is selected from liposoluble coenzyme Q10 or water-soluble coenzyme Q10.

Said drug combination is preferable to be oral or injective preparations, and preferably, the oral forms are selected from the group consisting of tablet, capsule, granule, pill, powder, solid dispersion, and oral liquid, while said injectable forms are selected from injection or lyophilized powder injection Beneficial Effect of the Present Invention In the present invention, based on the prior art, by large amount of screening studies, it is surprisingly to find that the combination of chlorogenic acid and adjuvant drugs with insignificant actions on amyotrophic lateral sclerosis realizes unexpected synergistic therapeutic effects on this disease, and the proportion of each drug has obviously influenced the therapeutic effect of the drug combination on amyotrophic lateral sclerosis. The screening in the present invention has shown the optimal ratio of chlorogenic acid, vitamin E, vitamin C, coenzyme Q10, and creatine phosphate sodium, and thus provided a drug combination with excellent therapeutic effect on amyotrophic lateral sclerosis, and can obviously delay the progression of amyotrophic lateral sclerosis.

Each ingredient in the drug combination for treatment of amyotrophic lateral sclerosis according to the present invention is safe, and doesn't have toxic side effects. Moreover, the preparative method of the drug combination is simple and suitable for industrial production.

EXAMPLES

Hereinafter, the present invention is more detailedly described to help understanding it.

Example 1: A Drug Combination for Treatment of Amyotrophic Lateral Sclerosis

The drug combination includes 300 mg unit preparation of chlorogenic acid, 500 mg unit preparation of vitamin E, 600 mg unit preparation of coenzyme Q10, and 2500 mg unit preparation of creatine phosphate sodium, and each unit preparation can be simultaneously or separately administrated.

Example 2: The Tablet for Treatment of Amyotrophic Lateral Sclerosis 300 g chlorogenic acid, 500 g vitamin E, 600 g vitamin C, 600 g coenzyme Q10, and 2500 g creatine phosphate sodium were processed according to the following method:

(1) Preparation of raw materials: each raw material was weighed according to the formula;

(2) Blending: chlorogenic acid, vitamin E, vitamin C, coenzyme Q10, and creatine phosphate sodium were mixed, to which were added microcrystalline cellulose, hydroxypropylmethylcellulose, and sodium carboxymethyl cellulose. The mixture was subjected to wet granulation, and after addition of magnesium stearate, the mixture was compressed into tablets. 10000 tablets in total were prepared, and each tablet contained 30 mg chlorogenic acid. Thus, the tablet of the present invention for treatment of amyotrophic lateral sclerosis was obtained.

Example 3: The Capsule for Treatment of Amyotrophic Lateral Sclerosis 180 g chlorogenic acid, 300 g vitamin E, 300 g vitamin C, 300 g coenzyme Q10, and 1000 g creatine phosphate sodium were processed according to the following method:

(1) Preparation of raw materials: each raw material was weighed according to the formula;

(2) Blending: chlorogenic acid, vitamin E, vitamin C, coenzyme Q10, and creatine phosphate sodium were mixed, to which were added microcrystalline cellulose, hydroxypropylmethylcellulose, and sodium carboxymethyl cellulose. The mixture was subjected to wet granulation, and after addition of magnesium stearate, the mixture was introduced into gelatin capsule shell. 6000 capsules in total were prepared, and each capsule contained 30 mg chlorogenic acid. Thus, the capsule of the present invention for treatment of amyotrophic lateral sclerosis was obtained.

Example 4: The Lyophilized Powder Injection for Treatment of Amyotrophic Lateral Sclerosis 100 g chlorogenic acid, 100 g tocopheryl polyethylene glycol succinate, 75 g vitamin C, 100 g water-soluble coenzyme Q10, and 500 g creatine phosphate sodium were processed according to the following method:

The materials in formula were dissolved in injectable water, and after filtration, the filtrate was further filtered with sterilized microporous membrane, and adjusted pH value. According to the general procedures for lyophilized powder injection, 2000 powder injections (2 ml) were prepared, and each injection contained 50 mg chlorogenic acid. Thus, the lyophilized powder injection of the present invention for treatment of amyotrophic lateral sclerosis was obtained.

Effect Example 1: Effect of the Drug Combination According to the Present Invention on Motor Function and Survival Time of Amyotrophic Lateral Sclerosis Mice 1.1 Experimental Drugs Positive control drug: Riluzole;

The drug combination 1 of the present invention: chlorogenic acid, vitamin E, vitamin C, coenzyme Q10, and creatine phosphate sodium, with a weight ratio of 180:300:300:300:500;

The drug combination 2 of the present invention: chlorogenic acid, vitamin E, vitamin C, coenzyme Q10, and creatine phosphate sodium, with a weight ratio of 180:300:300:300:1000;

The drug combination 3 of the present invention: chlorogenic acid, vitamin E, vitamin C, coenzyme Q10, and creatine phosphate sodium, with a weight ratio of 180:300:300:300:2000;

Control 1: chlorogenic acid
Control 2: chlorogenic acid, vitamin E, with a weight ratio of 180:300;
Control 3: chlorogenic acid, vitamin E, vitamin C, with a weight ratio of 180:300:300.
Control 4: chlorogenic acid, vitamin E, vitamin C, coenzyme Q10, with a weight ratio of 180:300:300:300;
Control 5: vitamin E, vitamin C, coenzyme Q10, creatine phosphate sodium, with a weight ratio of 300:300:300:1000;
Control 6: creatine phosphate sodium.

1.2 Experimental Animals and Experimental Method 10 two-months wild-type BALB/C mice were used as the normal control group, and 110 two-months hSOD1-G93A transgenic mice were randomly divided into 11 groups, 10 mice for each group, and 11 groups are blank group, positive control group, the drug compositions 1-3 of the present invention groups, and the control 1-6 groups, respectively.

All mice were adaptively fed for three weeks, and a rotating rod experiment was performed once a week. The diameter of the rotating rod was 3.5 cm, and its rotating speed was 12 r/min. Experiment on each mouse was carried out three times in parallel, with a 5 min interval. The longest time recorded was the fall time of mice, the mice with a fall time of shorter than 7 min in the third rotating rod experiment were excluded, and then mice received drugs by intragastric administration, in which the normal control group and the blank group were given physiological saline, while the positive control group, the drug combinations 1-3 groups, and the control groups 1-6 were given corresponding drugs, with the volume of 0.5 ml. Amongst, the gavage dose of positive control group was 2 mg/kg body weight, and the gavage dose of drug combinations 1-3 and controls 1-6 groups was both 40 mg/kg body weight. For all of groups, drugs were given once a day for 4 weeks. After 1 h of the 1st, 7th, 14th, 21st, and 28th intragastric administrations, a stick-rotation experiment was performed. In one experiment, each mouse was tested 3 times at interval of 5 minutes, and the longest time recorded was the fall time of mice. If mice did not fall after more than 10 min, the experiment was stopped and the fall time was recorded as 10 min. After the 28th gavage, the mice were continually fed, and the number of mice surviving for more than 120 days in each group was recorded, in which if they were placed in the supine position, the mice could not turn to the prone position within 30 S, and thus they were determined as dead. The detailed results are shown in Table 1.

1.3 Experimental Results

Data analysis was performed using multivariate ANOVA module of statistical software SPSS, and $P<0.05$ indicated that the difference was statistically significant.

The experimental results in Table 1 show that the hSOD1-G93A transgenic mice have the significantly reduced fall time on the first day of gavage compared to BALB/C mice, and the number of mice surviving more than 120 days in the experiment is also obviously lower than BALB/C mice, showing that with the progression of amyotrophic lateral sclerosis, hSOD1-G93A mice gradually lost their ability to exercise, that gradually caused the death of the mice.

TABLE 1

Effect of drug combinations on the motor function and the survival time of hSOD1-G93A mice

| Groups | Samples | Falling time (s) | | | | | Survival numbers |
|---|---|---|---|---|---|---|---|
| | | On 1$^{st}$ day of gavage | On 7$^{th}$ day of gavage | On 14$^{h}$ day of gavage | On 21$^{th}$ day of gavage | On 28$^{th}$ day of gavage | |
| Normal control group | 10 | 578.6 ± 3.2 | 600 | 600 | 600 | 600 | 10 |
| Blank group | 9 | 465.8 ± 21.6## | 290.2 ± 29.3## | 152.3 ± 21.3## | 67.1 ± 8.7## | 42.2 ± 4.8## | 2 |
| Positive control group | 8 | 479.2 ± 31.8 | 389.5 ± 27.7** | 259.3 ± 29.5** | 187.4 ± 17.5** | 129.3 ± 15.4** | 4 |
| Drug combination 1 of the present invention | 9 | 469.7 ± 25.9 | 412.6 ± 28.3** | 329.8 ± 23.2** | 228.3 ± 21.9** | 148.7 ± 16.6** | 5 |
| Drug combination 2 of the present invention | 9 | 482.1 ± 30.7 | 446.8 ± 26.4** | 365.3 ± 28.9** | 317.9 ± 24.3** | 226.3 ± 28.1** | 8 |
| Drug combination 3 of the present invention | 9 | 477.6 ± 27.3 | 422.4 ± 29.9** | 299.1 ± 26.4** | 257.3 ± 25.6** | 169.8 ± 23.2** | 6 |
| Control 1 | 8 | 468.9 ± 26.1 | 315.3 ± 27.6* | 221.5 ± 22.8** | 127.8 ± 19.5** | 89.1 ± 18.5** | 3 |
| Control 2 | 9 | 473.4 ± 23.9 | 322.6 ± 24.7* | 243.7 ± 28.2** | 149.1 ± 17.4** | 93.5 ± 16.7** | 4 |
| Control 3 | 8 | 474.8 ± 31.7 | 341.3 ± 25.1* | 239.2 ± 26.7** | 143.8 ± 28.3** | 109.7 ± 19.4** | 4 |

TABLE 1-continued

Effect of drug combinations on the motor function and the survival time of hSOD1-G93A mice

| Groups | Samples | Falling time (s) | | | | | Survival numbers |
| --- | --- | --- | --- | --- | --- | --- | --- |
| | | On $1^{st}$ day of gavage | On $7^{th}$ day of gavage | On $14^h$ day of gavage | On $21^{th}$ day of gavage | On $28^{th}$ day of gavage | |
| Control 4 | 8 | 466.7 ± 29.2 | 355.9 ± 28.6* | 245.7 ± 23.6** | 155.9 ± 22.4** | 112.2 ± 18.7** | 4 |
| Control 5 | 8 | 466.3 ± 24.0 | 293.8 ± 27.5 | 160.5 ± 18.4 | 77.6 ± 13.9 | 50.8 ± 9.7 | 2 |
| Control 6 | 9 | 475.8 ± 22.8 | 284.6 ± 19.3 | 155.8 ± 24.8 | 71.3 ± 12.3 | 44.78 ± 11.3 | 2 |

Compared to the normal control group:
$P < 0.01$; compared to the blank group:
*$P < 0.05$,
**$P < 0.01$.

After gavage of the positive control drug riluzole to hSOD1-G93A mice, the fall time of the mice in the rotating rod test was obviously longer than that of the mice in the blank group, and the number of mice surviving more than 120 days also increased from two mice in the blank group to four mice, showing that riluzole had the effect on delaying the progression of amyotrophic lateral sclerosis.

Gavage of chlorogenic acid, the combination of chlorogenic acid and vitamin E, the combination of chlorogenic acid, vitamin E, and vitamin C, the combination of chlorogenic acid, vitamin E, vitamin C, and coenzyme Q10 also showed to some extent the effect on delaying the progression of amyotrophic lateral sclerosis, in which the combination of chlorogenic acid, vitamin E, vitamin C, and coenzyme Q10 had an roughly equivalent effect on delaying the progression of amyotrophic lateral sclerosis as the positive control drug riluzole.

The mice in the group of the drug combinations 1-3 according to the present invention was given the drug combinations 1-3 via gavage, and their falling time was obviously elongated compared to the blank group, and the number of mice surviving more than 120 days also obviously increased, in which the indexes for the fall time of mice and the number of mice surviving more than 120 days were all better than those of mice in Riluzole group, proving that the drug combination of the present invention had an excellent effect on delaying the progression of amyotrophic lateral sclerosis.

By comparison of experimental results in the drug combinations 1-3 groups according to the present invention and in the controls 1-6 groups, it can be shown that although for the mice in the fifth control group with gavage of vitamin E, vitamin C, coenzyme Q10, and creatine phosphate sodium, together with those in the sixth control group with single gavage of creatine phosphate sodium, the indexes for the fall time and the number of mice surviving more than 120 days were roughly equivalent to those in the blank group, the indexes for the fall time and the number of mice surviving more than 120 days for the mice in the drug combinations 1-3 with addition of creatine phosphate sodium were both better than those in the fourth control group without creatine phosphate sodium, thus proving after addition of creatine phosphate sodium in the drug combination of chlorogenic acid, vitamin E, vitamin C, and coenzyme Q10, surprisingly, the effect of the drug combination on delaying the progression of amyotrophic lateral sclerosis was obviously improved. Creatine phosphate sodium don't have obvious effect on delaying the progression of this disease.

By comparison of experimental results in the drug combinations 1-3 groups according to the present invention, it can be shown that as the content increase of creatine phosphate sodium, the mice in the drug combination 2 group according to the present invention showed obviously better effect on delaying the progression of amyotrophic lateral sclerosis than that of mice in drug combination 1 group. Moreover, as further increase of the content of creatine phosphate sodium, the mice in the drug combination 3 group according to the present invention showed rather reduced effect on delaying the progression of amyotrophic lateral sclerosis, comparing to that of mice in drug combination 2 group. The reason may be that as further increase of the content of creatine phosphate sodium, the content of chlorogenic acid, vitamin E, vitamin C, and coenzyme Q10 in the drug combination will be reduced, and thus the content change of ingredients may influence the effect of the drug combination on delaying the progression of amyotrophic lateral sclerosis.

The preferred embodiments of the present invention have been described above, but they are not intended to limit the present invention. Those skilled in the art can make improvements and changes to the embodiments disclosed herein without department from the scope and spirit of the invention.

The invention claimed is:

1. A synergistic drug combination composition for treatment of amyotrophic lateral sclerosis consisting of the active ingredients: chlorogenic acid, vitamin E, vitamin C, coenzyme Q10 and creatine phosphate sodium in the weight ratio of 150-250:250-400:200-400:200-400:800-2000 and pharmaceutically acceptable carriers.

2. The drug combination for treatment of amyotrophic lateral sclerosis according to claim 1, wherein the weight ratio of chlorogenic acid, vitamin E, vitamin C, coenzyme Q10, and creatine phosphate sodium is 180:300:300:300:1000.

3. The drug combination for treatment of amyotrophic lateral sclerosis according to claim 1, wherein the drug combination is prepared as oral or injectable forms.

4. The drug combination for treatment of amyotrophic lateral sclerosis according to claim 3, wherein the oral forms are selected from the group consisting of tablet, capsule, granule, pill, powder, solid dispersion, and oral liquid, and the said injectable forms are selected from injection or lyophilized powder injection.

5. A method of preparing the drug combination for treatment of amyotrophic lateral sclerosis according to claim 1, wherein the drug combination is prepared by using chlorogenic acid, vitamin E, vitamin C, coenzyme Q10, and creatine phosphate sodium as active ingredients, together with addition of pharmaceutically acceptable carriers.

6. The method according to claim 5, wherein the drug combination is oral or injectable preparations.

7. A method for treatment of amyotrophic lateral sclerosis, comprising administering an effective amount of a composition of claim 1 to a subject in need thereof.

\* \* \* \* \*